US006912425B2

United States Patent
Nova et al.

(10) Patent No.: US 6,912,425 B2
(45) Date of Patent: Jun. 28, 2005

(54) THERAPY AND MONITORING ELECTRODES WITH PATIENT ACCOMMODATING FEATURES AND ELECTRODE SENSING

(75) Inventors: Richard C. Nova, Kirkland, WA (US); Kevin K. Covey, Marysville, WA (US); Joseph L. Sullivan, Kirkland, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 467 days.

(21) Appl. No.: 10/134,316

(22) Filed: Apr. 26, 2002

(65) Prior Publication Data

US 2003/0171798 A1 Sep. 11, 2003

Related U.S. Application Data

(63) Continuation-in-part of application No. 10/094,949, filed on Mar. 8, 2002.

(51) Int. Cl.[7] .............................................. A61N 1/05
(52) U.S. Cl. ..................................... 607/142; 607/148
(58) Field of Search ............................. 607/5, 142, 148, 607/152, 153; 600/382, 386, 389, 390, 393, 547

(56) References Cited

U.S. PATENT DOCUMENTS

| | | | | |
|---|---|---|---|---|
| 4,705,044 A | * | 11/1987 | Deluhery et al. | 607/142 |
| 4,895,169 A | * | 1/1990 | Heath | 607/142 |
| 5,080,099 A | * | 1/1992 | Way et al. | 600/391 |
| 5,366,497 A | * | 11/1994 | Ilvento et al. | 607/142 |
| 5,674,253 A | | 10/1997 | Adams et al. | |
| 5,817,151 A | | 10/1998 | Olson et al. | |
| 5,951,598 A | * | 9/1999 | Bishay et al. | 607/142 |
| 6,101,413 A | * | 8/2000 | Olson et al. | 607/5 |
| 6,125,298 A | * | 9/2000 | Olson et al. | 607/5 |
| 6,134,468 A | | 10/2000 | Morgan et al. | |
| 6,178,357 B1 | * | 1/2001 | Gliner et al. | 607/142 |
| 6,336,047 B1 | * | 1/2002 | Thu et al. | 607/5 |
| 6,374,137 B1 | * | 4/2002 | Morgan et al. | 607/5 |
| 6,567,697 B1 | * | 5/2003 | Kroll et al. | 607/5 |
| 6,714,824 B1 | * | 3/2004 | Ohta et al. | 607/142 |
| 6,799,063 B2 | * | 9/2004 | Carson | 600/372 |

* cited by examiner

*Primary Examiner*—Jeffrey R. Jastrzab
(74) *Attorney, Agent, or Firm*—Ingrassia Fisher & Lorenz PC

(57) ABSTRACT

Medical electrode arrangements are provided for electrotherapy and monitoring applications. In one embodiment, each electrode arrangement includes a smaller electrode that is releasably attached to the back of a larger electrode. For adult applications, the larger electrode is applied to the patient. For pediatric applications, the larger electrode is preferably removed, and the smaller electrode is applied to the patient. Face-to-face and back-to-back electrode arrangement configurations are also provided. In another embodiment, an electrode arrangement is comprised of first and second conductive regions that are separable from each other. In yet further embodiments, an electrode arrangement is comprised of two or more electrodes that are not physically or electrically connected to each other. At least one electrode from each electrode arrangement is placed on the patient. A sensor is also provided to sense which electrodes in each electrode arrangement have been placed on the patient.

46 Claims, 9 Drawing Sheets

THERAPY AND MONITORING ELECTRODES WITH PATIENT ACCOMMODATING FEATURES AND ELECTRODE SENSING

CROSS-REFERENCE TO RELATED APPLICATION

This application is a continuation-in-part of U.S. patent application Ser. No. 10/094,949, filed Mar. 8, 2002, entitled THERAPY AND MONITORING ELECTRODES WITH PATIENT ACCOMMODATING FEATURES.

FIELD OF THE INVENTION

The present invention relates generally to electrotherapy methods and apparatus. More particularly, the present invention relates to electrode configurations for electrotherapy and monitoring devices, and to sensing the electrode configuration placed on a patient.

BACKGROUND OF THE INVENTION

Electrotherapy (e.g., defibrillation, cardioversion, and pacing) is commonly applied to patients suffering from cardiac arrest and other cardiac arrhythmias. Conventionally, electrotherapy has been applied using "hard paddles" sized appropriately for the individual undergoing treatment. Some paddle designs have integrated two or more paddle sizes utilizing clip-or slide-on/off adapters of larger or smaller size. More commonly today, "soft paddle" products are used, which provide single-use, disposable, conductive adhesive electrode pads for arrhythmia monitoring and therapy delivery. Multiple-size soft paddles or pads are offered for varying sized patients. Sizes are commonly classified for use by age or weight of the patient.

Electrotherapy devices, such as defibrillators, are becoming more widespread. This has been driven in part by the introduction and acceptance of automated external defibrillators or AEDs. AEDs are used by first responders such as police officers, firefighters, and emergency medical technicians to resuscitate victims of sudden cardiac arrest. Studies have shown that the chances of successfully resuscitating a patient decrease approximately 10 percent per minute following the onset of sudden cardiac arrest. Accordingly, for a victim of sudden cardiac arrest, time is of the essence in defibrillating the patient's heart.

AEDs are designed to be very easy to use so that rescuers without extensive medical training can provide defibrillation therapy to victims of sudden cardiac arrest. AEDs are currently carried in emergency vehicles such as police cars, paramedic vehicles, and fire trucks. AEDs are also widely deployed in areas where large numbers of people gather, such as at sports stadiums, gambling casinos, theme parks, etc. As AEDs have evolved, they have become more and more intuitive to use and are now being used by individuals with limited or no medical training. This trend is expected to continue.

AEDs almost exclusively use soft paddles for therapy delivery. At the present time, however, AEDs are also almost exclusively used on adults and are recommended only for use on patients that are 8 years old or greater. Although cardiac arrest occurs predominantly in adults, circumstances arise in which defibrillation therapy is medically indicated for children. Consequently, there is a need for defibrillator devices, especially AEDs, to have pediatric capabilities.

Soft electrode pads sized for pediatric patients are available for use with manual defibrillators. As AED designs become adapted for pediatric delivery in terms of ECG recognition and therapy dosing, the pediatric pads available today can be utilized for pediatric defibrillation and resuscitation. However, there is resistance to adding small-sized, disposable electrode pad sets to AEDs, principally due to the added cost, packaging limitations, significantly lower likelihood of use, and limited shelf-life of the electrodes. Multiple separate electrode sets with separate connectors may also be confusing to untrained users.

Some users, when faced with the need for pediatric defibrillation and resuscitation, cut down larger pads for use on children and newborns. Although a creative approach, this method can compromise the therapy delivered due to uncontrolled altering of the current distribution area of the pad, along with the potential reduction of adhesive coupling of the pad to the skin. In addition, the safety characteristics of the electrode pad are compromised by removal of some of the insulative portion of the pad that commonly surrounds the conductive area.

There is, therefore, a need for a disposable electrode pad set that can easily be adapted for use on varying sized patients at a usage cost and package size below that of multiple individual sets, with greater convenience. There is also a need for a system that senses the configuration of the electrode pads placed on a patient for controlling the therapy delivery to the patient. The present invention is directed toward satisfying these needs and other shortcomings in the prior art.

SUMMARY OF THE INVENTION

The present invention is directed to multi-electrode pad arrangements and electrode sensing for providing electrotherapy/monitoring to patients of varying size or age. In certain embodiments of the invention, the electrode arrangements have a larger electrode suitable for use in treating an adult-size patient and a smaller electrode suitable for use in treating a pediatric-size patient. The larger electrode is attached to the smaller electrode in a front-to-front, back-to-back, or front-to-back configuration.

Other embodiments of the invention include electrode arrangements having adult and pediatric electrodes that are not attached to each other. Each electrode in an electrode arrangement is adhereable to different size patients, (e.g., an adult or pediatric patient) and includes a conductive surface area adapted for placement on the patient. The conductive surface areas of each electrode are protected from inadvertent adhesion and premature deterioration by a nonconductive release liner or by the physical attachment of one electrode to the other (e.g., the small electrode being releasably attached to a nonconductive backing substrate of the other electrode).

For embodiments in which the electrodes in an electrode arrangement are connected to each other, if adult treatment is required, the smaller pediatric electrode may be removed from the electrode arrangement, with the larger electrode being placed on the patient. Likewise, for pediatric treatment, the larger adult electrode may be removed from the electrode arrangement, with the smaller electrode being placed on the patient. In some embodiments, the conductive surface areas of each electrode in the electrode arrangements are initially electrically connected to one another. The separation of one electrode from the other preferably breaks the electrical connection between the conductive surface areas of the electrodes.

An electrode arrangement according to the present invention may also be comprised of an electrically nonconductive substrate having a first region that is coplanar with a second region. Each of the first and second regions of the electrode arrangement have a conductive surface area disposed thereon and, depending on the particular embodiment, the conductive surface areas of the first and second regions may be electrically connected to one another. The electrode arrangement is constructed such that the first and second regions are separable by a user of the electrode arrangement.

Prior to use, a nonconductive release liner preferably protects the conductive surface areas from inadvertent adhesion and premature deterioration. When treating an adult, the release liner is discarded and the conductive surface areas of both the first and second regions of the electrode arrangement are placed on the patient. When treating a pediatric patient, the second region of the electrode arrangement is separated from the first region and discarded. The first region of the electrode arrangement is then placed on the pediatric patient. The first and second regions of the electrode arrangement may be separated along a division line that includes perforations or is otherwise weakened by crimping or scoring.

One aspect of the present invention provides a sensing mechanism for an electrotherapy or monitoring apparatus to detect which of the electrodes in the electrode arrangements are attached to the patient. Given knowledge of the electrode configuration that is used (e.g., which of the adult or pediatric electrodes have been placed on the patient), the device may modify its output display in order to reflect the electrode configuration being used. For instance, when pediatric defibrillation is desired, the defibrillator detects that the pediatric electrodes in each electrode arrangement have been placed on the patient and modifies its energy output display to reflect the fact that pediatric electrodes are in use. This improved display can be achieved with or without the defibrillation device altering the energy protocol that it uses for therapy delivery.

In another aspect of the present invention, an energy attenuator is provided so that energy delivered to a patient through designated pediatric electrodes is less than the energy delivered through electrodes designated for adults. In one embodiment, the energy attenuator is a resistive component placed in series with the pediatric electrode in each electrode arrangement. The resistive component dissipates a portion of the electrical energy transferred from the defibrillator before it reaches the patient. In another embodiment, an energy attenuator is provided in the form of a resistor network attached across the pediatric electrodes in the electrode arrangements to reduce the amount of electrical energy transferred through the pediatric electrodes.

An electrical signal may be used to sense which electrodes in the electrode arrangements have been placed on the patient. The electrical signal is communicated through each of the electrodes in the electrode arrangements. The device determines which electrodes have been placed on the patient by identifying which electrodes form an electrical path through the patient.

The electrode arrangements are preferably configured so that electrodes with corresponding characteristics are placed on the patient. If an improper combination of electrodes is sensed on the patient (e.g., two electrodes from one electrode arrangement and one electrode from another electrode arrangement), a fault condition may be reported to the user of the device. The report may be accompanied by a prompt that instructs the user to correct the electrode placement.

Another advantage of the present invention is that the electrotherapy to be delivered to the patient may be adjusted based on which electrodes in each electrode arrangement have been placed on the patient. Certain combinations of electrodes on the patient may signal an adult patient while other combinations of electrodes may signal a pediatric or infant patient. The device may report the particular type of patient to the user. Furthermore, aspects of the electrotherapy, such as energy dosage, duration, peak current and/or peak voltage may be adjusted depending on which electrodes have been placed on the patient.

Electrode arrangements constructed in accordance with the present invention thus enable caregivers to select an electrode configuration for different size patients in a manner that is less confusing and at lower cost.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
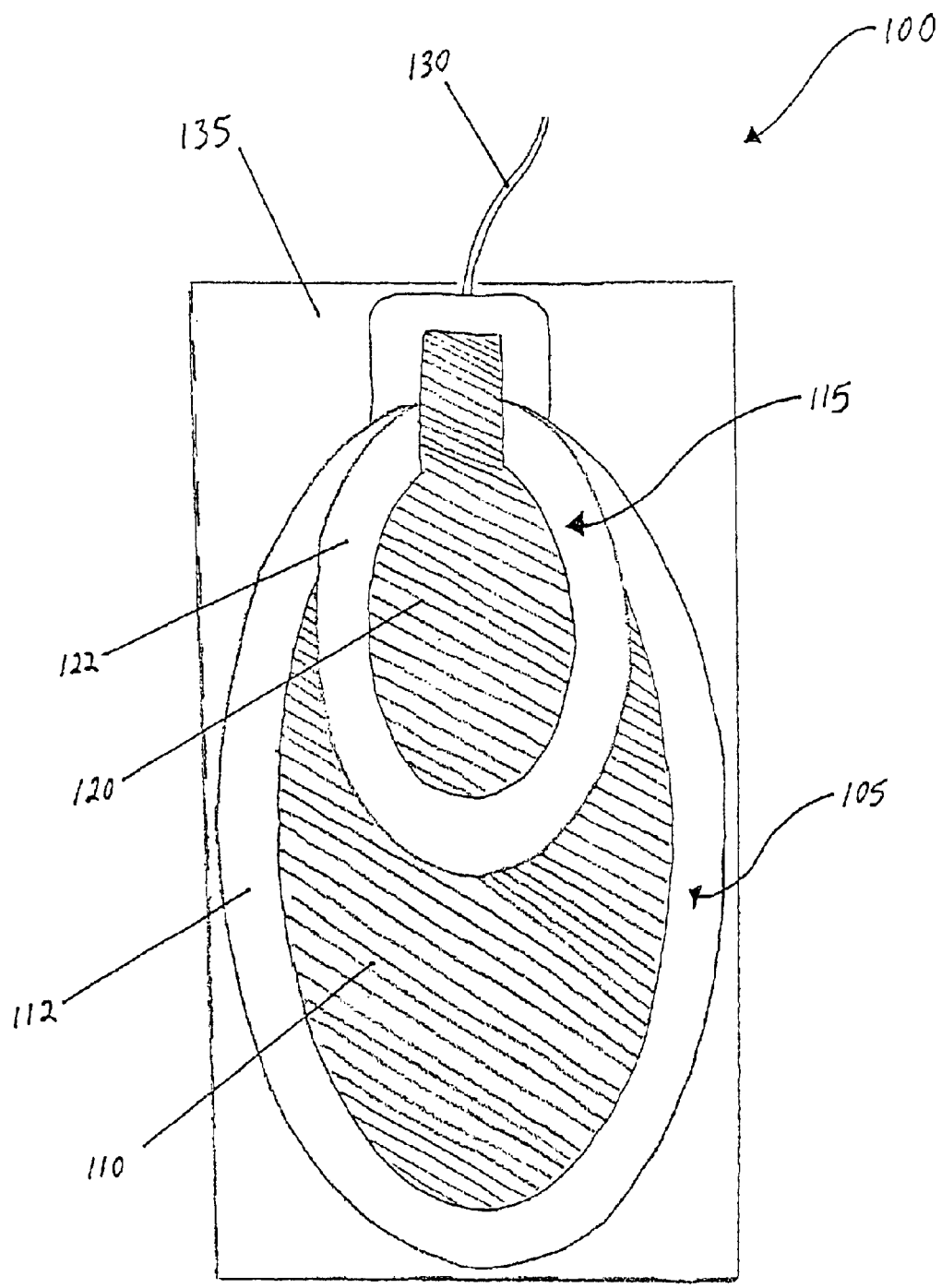
FIG. 1 is a plan view of an electrode arrangement configured according to one embodiment of the present invention.

FIG. 1 depicts an electrode arrangement 100 constructed in accordance with one embodiment of the present invention. The electrode arrangement 100 includes a smaller electrode 115, suitable for pediatric use, releasably attached to a nonconductive backing substrate of a larger electrode 105, suitable for use on an adult. Each electrode 105 and 115 has a conductive surface area 110 and 120, respectively, preferably including a conductive gel, that is used to conduct electrical energy to a patient. In this embodiment of the invention, the conductive surface area 120 is smaller than the conductive surface area 110, though that is not required.

A region of adhesive 122 surrounds some or all of the conductive surface area 120 to adhere the smaller electrode 115 to a pediatric patient. Similarly, adhesive region 112 surrounds some or all of the conductive surface area 110 to adhere the larger electrode 105 to an adult patient. A nonconductive release liner 135 is releasably attached to the bottom of the larger electrode 105 to cover the adhesive 112 and conductive surface area 110, preventing deterioration of the conductive gel and/or accidental attachment of the electrode 105 prior to use. An electrical lead wire 130 is used to couple the electrode arrangement 100 to a defibrillator or other electrotherapy device or monitor.

Electrotherapy and monitoring applications typically require two or more electrodes to be placed on the patient. For example, an electrode may be placed in an anterior position and another electrode in a posterior position on the patient. In another application, an electrode may be placed in an apex position and another electrode may be placed in a sternum position. In context of the latter application, an electrode arrangement described herein provides two or more electrodes for the apex position and another electrode arrangement provides two or more electrodes for the sternum position. Thus, two electrode arrangements provided by the present invention would be used. More than two electrode arrangements may be used in other applications. The particular electrode or electrodes in each electrode arrangement that are placed on the patient depends on the patient and may be determined based on the age or size of the patient.

Moreover, it should be understood that the terms "adult" and "pediatric" as used herein are not meant to be limiting to any specific age group or patient size. Rather, the terms "adult" and "pediatric" are merely indicators that identify general patient types for whom one or more electrodes in each electrode arrangement may be best suited. The term "infant" is also used herein in a nonlimiting manner and may be a patient type separate from or included in the "pediatric" patient type.

In terms of FIG. 1, when performing cardiac defibrillation on an adult, the release liner 135 is removed from the bottom of the larger electrode 105, exposing both the adhesive region 112 and the conductive gel 110. The electrode 105 is applied to the skin of the adult patient, and electrical energy is conducted to the patient through the conductive gel 110 from an AED or other defibrillation device. In this case, the smaller electrode 115, along with its conductive gel 120 and adhesive 122, is simply "along for the ride" and performs no active role in the defibrillation.

When cardiac defibrillation on a pediatric patient is required, the smaller electrode 115 is peeled away from the backing substrate of the larger electrode 105 and applied to the patient. In this manner, the backing substrate of the larger electrode 105 effectively acts as a nonconductive release liner for the smaller electrode 115. The electrical lead wire 130 remains coupled to the smaller electrode 115 while the electrical coupling to the larger electrode 105 preferably tears away. The unused larger electrode 105 is discarded, and electrical energy from an AED or other defibrillation device is conducted to the patient through the conductive gel 120 of the smaller electrode 115.

Figure 2:
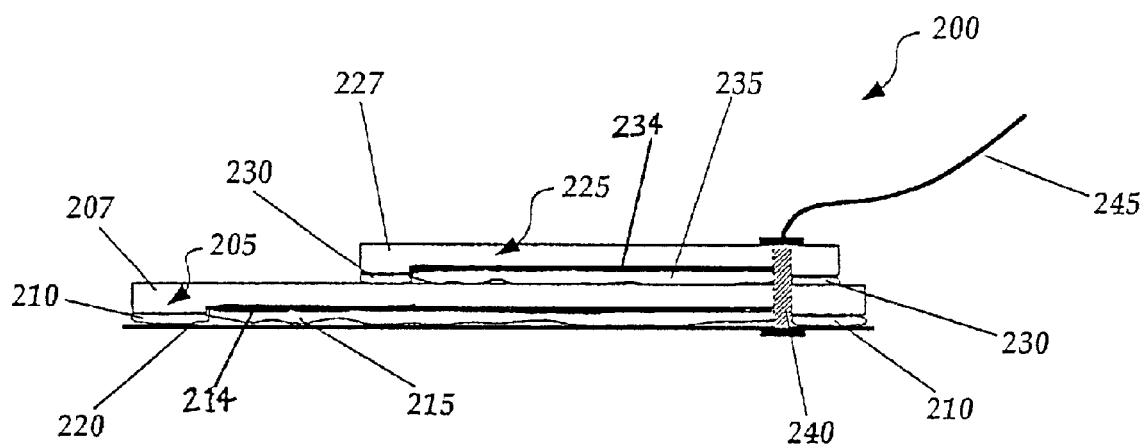
FIG. 2 is a cross-sectional transverse view of the electrode arrangement shown in FIG. 1.

FIG. 2 depicts a cross-sectional transverse view of an electrode arrangement 200 constructed as shown in FIG. 1. A smaller electrode 225, having a nonconductive backing substrate 227, is releasably attached via adhesive 230 to a nonconductive backing substrate 207 of a larger electrode 205. In turn, the larger electrode pad 205 is releasably attached via adhesive 210 to a nonconductive release liner 220. In a preferred embodiment, the nonconductive backing substrate 207 is treated with a release coating, at least in the area where the smaller electrode 225 is attached, to facilitate the release of the smaller electrode 225 from the larger electrode 205.

A plate 234 made of conductive material is preferably disposed in a central region of the smaller electrode 225. Similarly, a conductive plate 214 is preferably disposed in a central region of the larger electrode 205. Conductive gels 235 and 215 cover the conductive plates 234 and 214 respectively, and preferably cover the entire exposed area of the conductive plates 234, 214. The conductive plates 234, 214 and the conductive gels 235, 215 comprise the conductive surface areas of the smaller electrode 235 and larger electrode 205, respectfully, and distribute the electrical energy delivered to the patient. A lead wire 245, adapted to connect to an AED or other electrotherapy or monitoring device, is electrically coupled to the conductive plate 234 and the conductive plate 214 through a conductive connector 240.

As discussed above in regard to FIG. 1, when adult defibrillation is required, the nonconductive release liner 220 is peeled away from the larger electrode 205 and the larger electrode is attached to the patient. The lead wire 245 is attached to an AED or other defibrillation device. Defibrillation energy is then conducted to the patient through the lead wire 245, the conductive connector 240, the conductive plate 214, and conductive gel 215. The smaller electrode 225, while still electrically connected to the conductive connector 240, performs no active role in the defibrillation as it remains attached to the nonconductive backing substrate 207 of the larger electrode 205.

Figure 3:
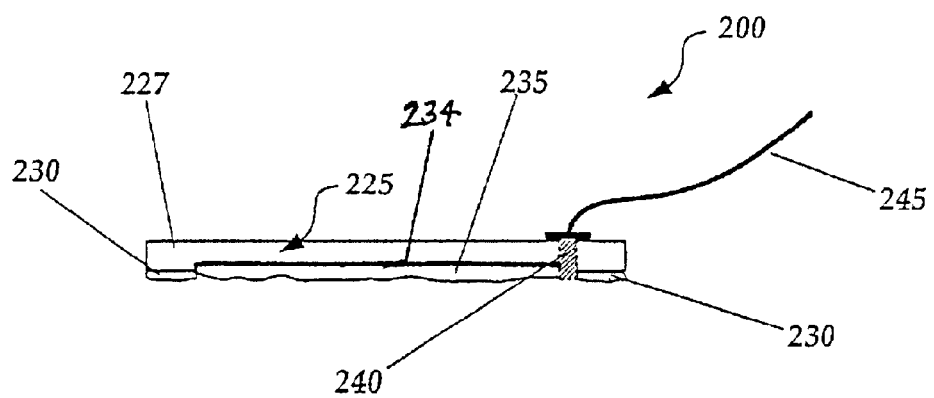
FIG. 3 is a cross-sectional transverse view of the electrode arrangement shown in FIG. 1, depicting use as a pediatric defibrillator electrode, wherein the larger adult electrode pad has been removed.

When pediatric defibrillation is required, the larger electrode 205 with release liner 220 is peeled away from the smaller electrode 225, preferably breaking the electrical coupling of connector 240 to the larger electrode 205. As shown in FIG. 3, the larger adult electrode 205 (FIG. 2) has been removed from the electrode arrangement 200 and discarded. This allows the smaller electrode 225 to be attached to a pediatric patient via adhesive 230 and gel 235. Defibrillation energy is then delivered to the patient from an AED or other defibrillation device through the lead wire 245, the conductive connector 240 that remains, the conductive plate 234, and conductive gel 235.

As is evident from the foregoing, until the larger electrode 205 is removed from the smaller electrode 225, the conductive surface areas of the respective electrodes are electrically connected via the conductive connector 240. If the larger electrode 205 is peeled away from the smaller electrode 225, the electrical connection between the electrodes is broken, as illustrated, for example, in FIG. 3. In that circumstance, only the smaller electrode 225 is placed on the patient.

Figure 4:
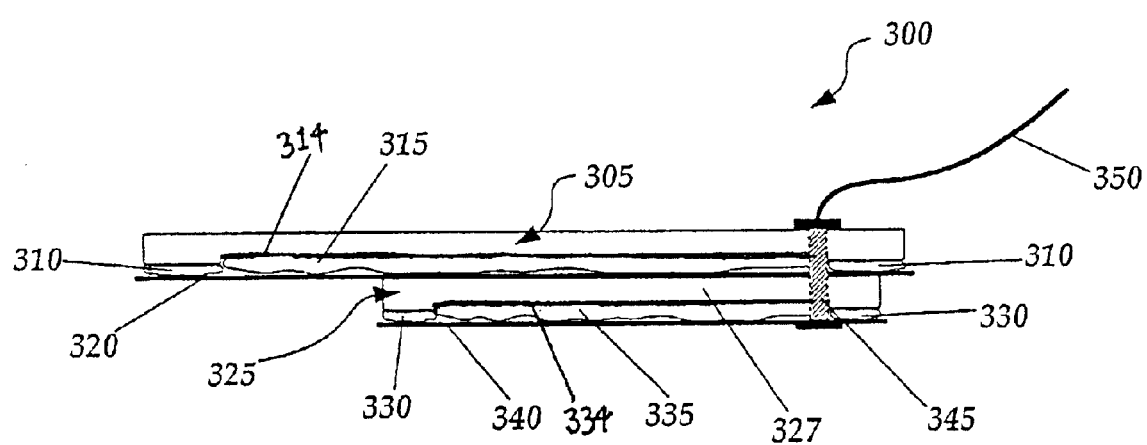
FIG. 4 is a cross-sectional transverse view of an electrode arrangement configured according to another embodiment of the present invention.

FIG. 4 illustrates an electrode arrangement 300 constructed in accordance with another embodiment of the present invention. A larger electrode 305, having a conductive plate 314 and conductive gel 315, is releasably attached via adhesive 310 to a nonconductive release liner 320 that covers the conductive gel 315. The opposite side of the nonconductive release liner 320 is attached to a nonconductive backing substrate 327 of a smaller electrode 325. The smaller electrode 325 is in turn releasably attached to a smaller nonconductive release liner 340 via adhesive 330. The nonconductive release liner 340 covers the conductive gel 335 and conductive plate 334 of the smaller electrode 325.

As with the other embodiments of the invention discussed above, when adult defibrillation is required, only the larger electrode 305 is utilized. The electrode 305 is peeled away from the nonconductive release liner 320 and smaller electrode 325, preferably breaking the electrical coupling of the smaller electrode 325 to the conductive connector 345. The nonconductive release liner 320 is discarded along with the smaller electrode 325. Defibrillation energy is delivered to the patient through the lead wire 350, conductive connector 345, conductive plate 314, and conductive gel 315.

When pediatric defibrillation is needed, however, the smaller nonconductive release liner 340 is removed, exposing adhesive 330 and conductive gel 335 for application to the patient. Defibrillation energy is delivered to the pediatric patient through the lead wire 350, conductive connector 345, conductive plate 334, and conductive gel 335. The larger electrode 305, while still connected to the nonconductive release liner 320 and smaller electrode 325, is only "along for the ride" and performs no active role in the defibrillation.

Recognizing that in some pediatric applications there may not be sufficient space on the patient for the electrodes when the larger electrode 305 remains attached to the smaller electrode 325, the electrode arrangement 300 may be configured to permit detachment of the larger electrode 305 when pediatric defibrillation is needed. In that circumstance, the electrode arrangement 300 is constructed so that the lead wire 350 remains connected to the smaller electrode 325 after the larger electrode 305 is removed. In that regard, an exemplary embodiment provides perforations in the larger electrode 305 to assist in detaching the larger electrode 305.

Figure 5:
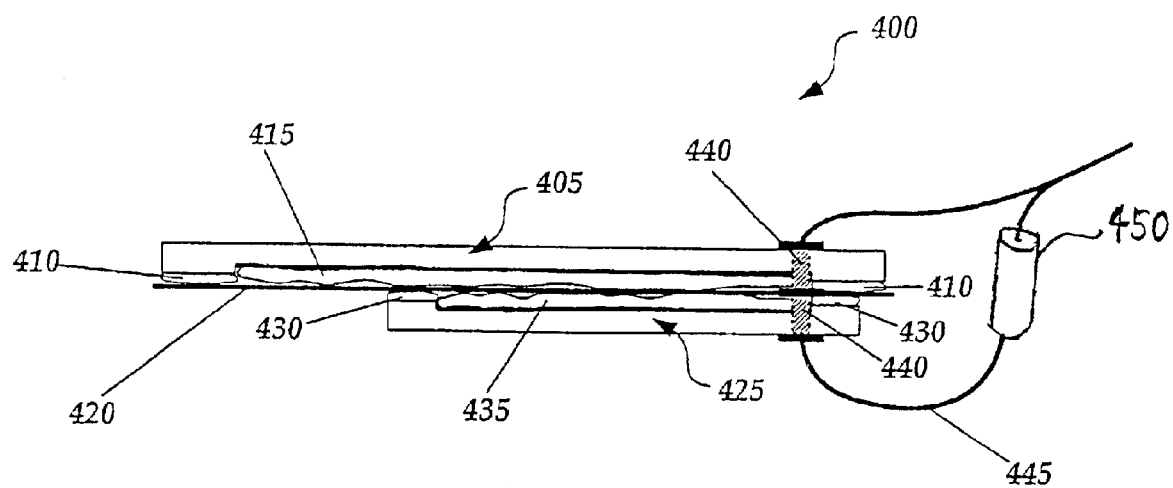
FIG. 5 is a cross-sectional transverse view of an electrode arrangement configured according to yet another embodiment of the present invention.

FIG. 5 illustrates yet another embodiment of the present invention in which electrodes in electrode arrangement 400 are arranged in a face-to-face configuration. A nonconductive release liner 420 is disposed between larger electrode 405 and smaller electrode 425, both of which are adhered to opposing sides of the release liner 420 via adhesive 410 and 430, respectively. The release liner 420 is sized to cover the face of both electrodes 405 and 425 to prevent conductive gels 415 and 435 from inadvertent attachment and premature deterioration. Lead wire 445 divides into two wires that are connected to each of the larger and smaller electrodes 405 and 425.

When adult defibrillation is required, the release liner 420 is peeled away from the larger electrode 405, and, along with smaller electrode 425, is placed away from the patient. The larger electrode 405 is then attached to the patient via adhesive 410 and gel 415. If, however, pediatric defibrillation is needed, the release liner 420 is peeled away from the smaller electrode 425, and, along with the larger electrode 405, is placed away from the patient. The smaller electrode 425 is then attached to the patient via adhesive 430 and gel 435. For either an adult or pediatric patient, defibrillation therapy is then provided by conducting electrical energy through lead wire 445, conductive connector 440, and the conductive plate and gel of the electrode 405 or 425 that is attached to the patient.

In FIG. 5, the smaller electrode 425 is also shown with an optional energy attenuator 450 that is configured to reduce the amount of electrical energy transferred to the patient through the electrode 425. The energy attenuator 450 may comprise one or more resistors that scale the energy delivered to an amount appropriate for pediatric applications. Alternatively, energy attenuation may be provided by a resistor network attached across the smaller (pediatric) electrodes in two or more electrode arrangements, as described below in more detail in reference to FIG. 12.

The electrode arrangement 400 may also be configured to use both electrodes 405 and 425 for adult defibrillation and only electrode 425 for pediatric defibrillation. In this configuration, the electrodes 405 and 425 are removed from the release liner 420 but remain electrically connected via the divided lead wire 445 which conducts electrical energy to both electrodes simultaneously. Adding the conductive area of the smaller electrode 425 to the conductive area of the larger electrode 405 may be particularly advantageous for large adult patients.

Figure 6:
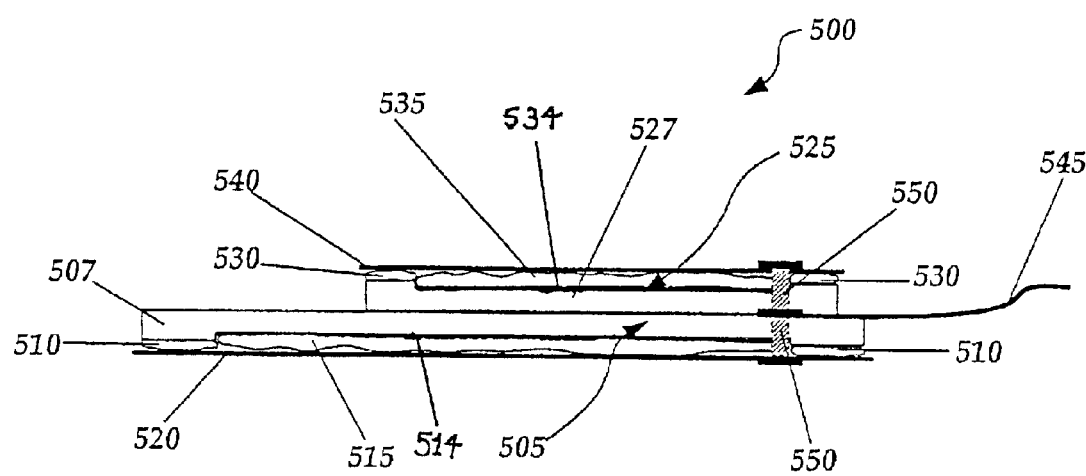
FIG. 6 is a cross-sectional transverse view of an electrode arrangement configured according to still another embodiment of the present invention.

FIG. 6 illustrates yet another embodiment of the present invention in which electrodes in electrode arrangement 500 are arranged in a back-to-back configuration. More specifically, a nonconductive backing substrate 527 of a smaller electrode 525 is attached to a nonconductive backing substrate 507 of a larger electrode 505. A nonconductive release liner 540 is attached to the smaller electrode 525, covering conductive gel 535. As for the larger electrode 505, a nonconductive release liner 520 is attached and covers conductive gel 515. A lead wire 545 is preferably coupled to the electrodes 505 and 525 between the respective backing substrates 507 and 527.

When pediatric defibrillation is contemplated, the nonconductive liner 540 is removed from the smaller electrode 525, exposing the conductive gel 535. The smaller electrode 525 is attached to the patient via adhesive 530. Defibrillation energy is then conducted through the lead wire 545, conductive connector 550, conductive plate 534, and conductive gel 535 to the patient.

When adult defibrillation is needed, however, the nonconductive liner 520 is removed, exposing the conductive gel 515. The larger electrode 505 is attached to the patient via adhesive 510. Defibrillation energy is then conducted to the patient via lead wire 545, conductive connector 550, conductive plate 514, and conductive gel 515.

In FIG. 6, the backing substrate 527 of the smaller electrode 525 may be releasably attached to the backing substrate 507 of the larger electrode 505, so that in use, the unused electrode may be removed and discarded. This configuration is advantageous in that it permits the unused electrode to be removed. For example, the larger electrode 505 may be removed in pediatric applications where there is not enough space on the pediatric patient to accommodate the larger, unused electrode 505. Alternatively, the connection between the electrode backing substrates 507 and 527 may be permanent, in which case the nonconductive release liners 520 and 540 are constructed to protect the user from unintended shocks from the unused electrode. In a further embodiment, the backing substrates 507 and 527 may be integrated to form a single nonconductive substrate with an adult (e.g., larger) conductive surface area 515 on one side and a pediatric (e.g., smaller) conductive surface area 535 on the other side.

Figure 7:
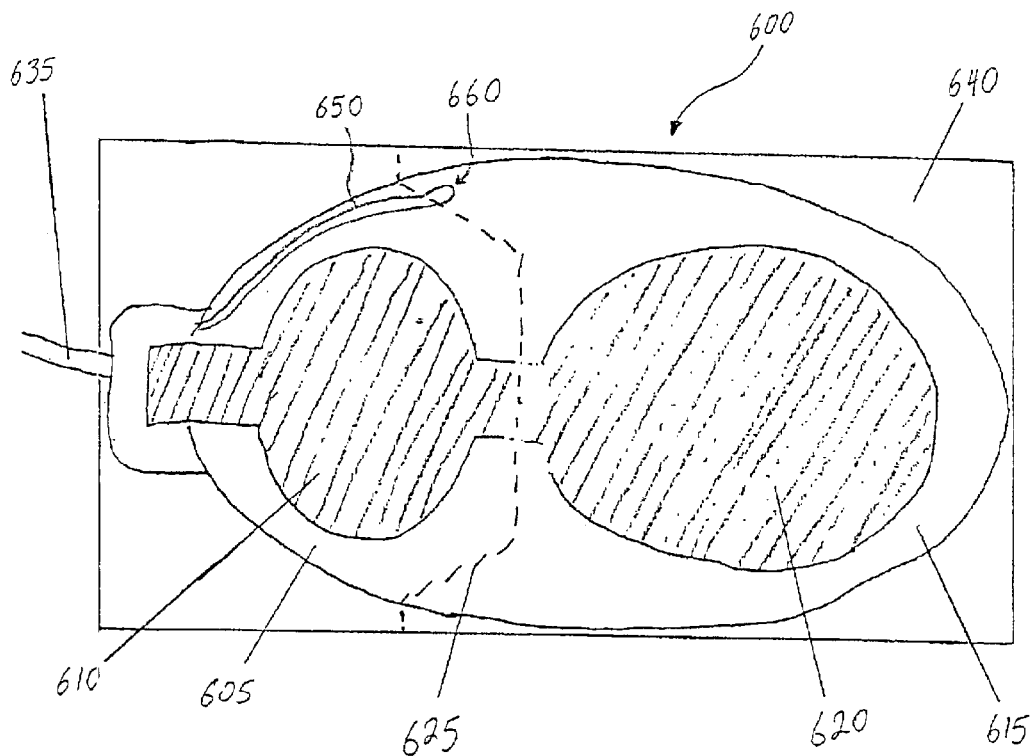
FIG. 7 is a plan view of an electrode arrangement configured according to a further embodiment of the present invention.
Figure 8:
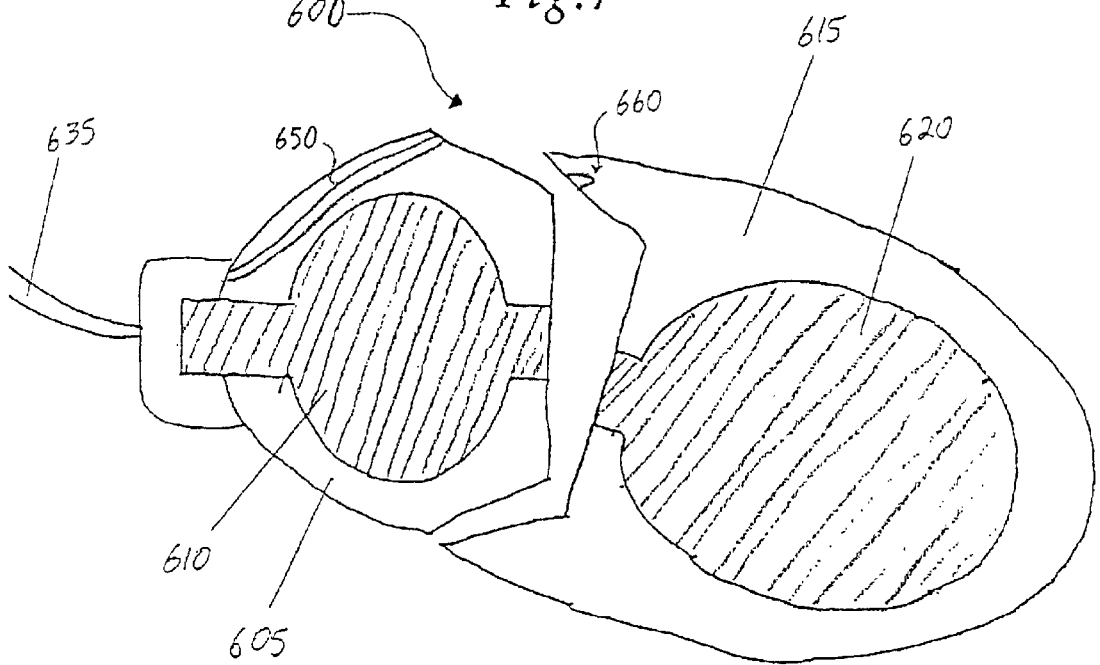
FIG. 8 is a plan view of the electrode arrangement shown in FIG. 6, depicting use as a pediatric defibrillator electrode, wherein an electrode section has been removed.

Referring to FIGS. 7 and 8, in still another embodiment of the invention, an electrode substrate in a common plane is divided into a first electrode section 605 and a second electrode section 615 along division line 625. Division line 625 may be formed via perforation, scoring, crimping, or other method of weakening the substrate material for the purpose of guided physical separation. Conductive surface areas 610 and 620 are disposed on each of the first electrode section 605 and second electrode section 615, respectively, and are electrically coupled to each other. A lead wire 635 is electrically connected to the conductive surface area 610.

In combination, the conductive surface areas 610, 620 are sized to provide a single adult electrode, while the single conductive surface area 610, located in the first electrode section 605 proximal to the lead wire 635, is sized to provide a single pediatric electrode. An adhesive appropriate for attachment to a patient is disposed on the portion of the electrode substrate outside the conductive surface areas 610, 620. A nonconductive release liner 640 is releasably attached to the conductive surface areas 610, 620 to prevent inadvertent attachment of the electrodes and protect the conductive gel.

To provide adult defibrillation, the release liner 640 is peeled away from the electrode sections, exposing conductive surface areas 610 and 620 which are placed on the patient. Defibrillation energy from an AED or other defibrillation device is conducted through the lead wire 635 and both conductive surface areas 610, 620 to the patient. If, however, pediatric defibrillation is desired, the second electrode section 615, distal to the attachment of lead wire 635, is separated along division line 625 and discarded, thus breaking the electrical connection between the conductive surface areas 610, 620. The first electrode section 605, along with its conductive surface area 610, remains coupled to the lead wire 635 and, after removal of the release liner 640, is applied to the patient. Defibrillation therapy may then be delivered to the pediatric patient. FIG. 8 displays the discarded second electrode section 615 as removed from the first electrode section 605.

A further aspect of the present invention enables the defibrillation or monitoring device attached to the electrode arrangements to detect which electrode(s) in each electrode arrangement are being used. Referring once again to FIG. 7, one exemplary detection mechanism includes a wire 650 forming a current path in the first electrode section 605. The wire 650 is attachable to the defibrillation or monitoring device via an electrical connection in lead wire 635 that is separate from the electrical connection in lead wire 635 to the conductive surfaces areas 610, 620. A loop in the wire 650 forms a circuit closure 660, located in second electrode section 615. An alternative circuit closure 660 includes a separate conducting plate in the second electrode section 615, which electrically connects the ends of the wire 650 when the second electrode section 615 is connected to the first electrode section 605.

When using the electrode arrangement 600 for adult defibrillation, both sections 605, 615 remain connected as described above, and circuit closure 660 provides a short-circuit termination to the wire 650. When using the electrode arrangement 600 for pediatric defibrillation, as shown in FIG. 8, the connection with wire 650 is broken and circuit closure 660 is removed and discarded along with second electrode section 615. The wire 650 therefore terminates in an open circuit. This difference in terminating impedance allows an external defibrillation or monitoring device to detect the configuration of the electrode arrangement 600 that is being used: a closed circuit, or zero impedance, in the wire 650 indicates an adult configuration while an open circuit, or high impedance, in the wire 650 indicates a pediatric configuration.

Figure 9:
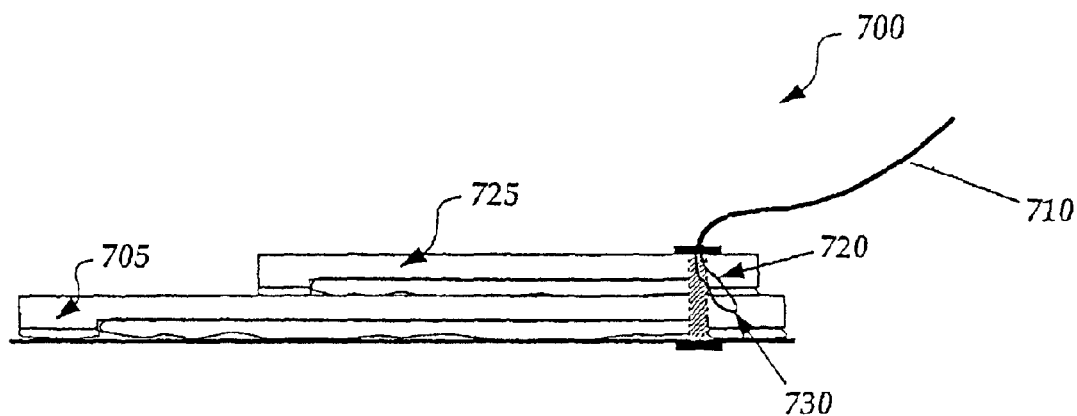
FIG. 9 is a cross-sectional transverse view of the electrode arrangement shown in FIGS. 1 and 2, and includes a sensing mechanism for detecting the configuration in use.

Referring to FIG. 9, an electrode arrangement 700 as shown in FIGS. 1 and 2 provides a similar exemplary sensing mechanism that includes a wire 720 forming a current path attached to a separate electrical connection within lead wire 710. The wire 720 extends through smaller electrode 725 to connect with circuit closure 730, in larger electrode 705. When using the electrode arrangement 700 for adult defibrillation, the circuit closure 730 provides a short-circuit termination for the wire 720. When pediatric defibrillation occurs, however, the connection with wire 720 is broken and the larger electrode 705 is removed and discarded along with the circuit closure 730. The wire 720 therefore terminates in an open circuit, detectable by the defibrillation or monitoring device, indicating a pediatric configuration for the electrode arrangement 700.

Figure 10:
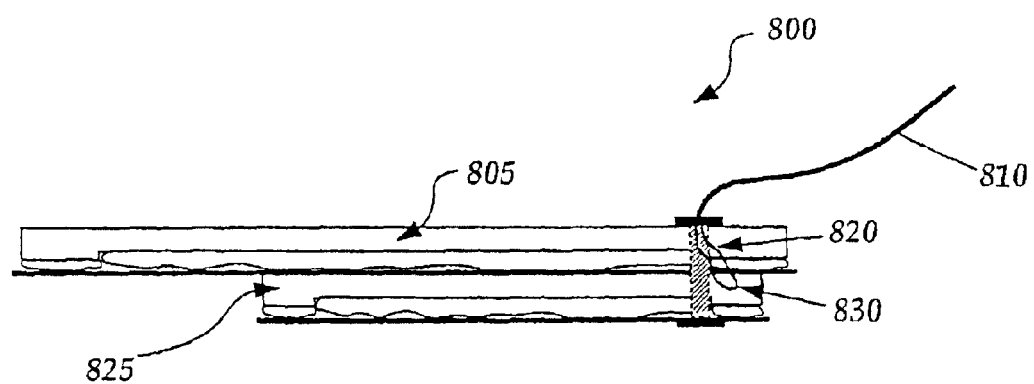
FIG. 10 is a cross-sectional transverse view of the electrode arrangement shown in FIG. 4 including a sensing mechanism for detecting the configuration in use.

In another electrode arrangement 800, shown in FIG. 10, larger electrode 805 is positioned on the back of smaller electrode 825, such as shown and described in FIG. 4. A sensing mechanism includes a wire 820 forming a current path attached to a separate electrical connection within lead wire 810. The wire 820 extends through the larger electrode 805 to connect with circuit closure 830, which may be a loop in the wire 820, in the smaller electrode 825. When using the electrode arrangement 800 for pediatric defibrillation, the circuit closure 830 provides a short-circuit termination for the wire 820. When adult defibrillation occurs, however, the connection with wire 820 is broken and the smaller electrode 825 is removed and discarded along with the circuit closure 830. The wire 820 therefore terminates in an open circuit, again detectable by the defibrillation or monitoring device, indicating an adult configuration for the electrode arrangement 800.

A sensing mechanism as described above may also be incorporated into the electrode arrangements shown in FIGS. 5 and 6. In FIG. 5, a sensing wire as described above (not illustrated) may extend through the smaller electrode 425 and connect with a circuit closure in the nonconductive liner 420. When adult defibrillation is performed, the larger electrode 405 is used and the liner 420 remains attached to the smaller electrode 425, maintaining a closed circuit in the sensing wire. When pediatric defibrillation is performed, the liner 420 is removed from the smaller electrode 425, breaking the connection with the sensing wire and resulting in an open circuit that is detectable by the defibrillation or monitoring device to indicate a pediatric electrode configuration.

Similarly, with the electrode arrangement 500 shown in FIG. 6, a sensing wire as described above may extend through the smaller electrode 525 and connect with a circuit closure in the nonconductive liner 540. Removal of the liner 540 for a pediatric application results in an open circuit in the sensing wire. For an adult application, the nonconductive liner 520 is removed while liner 540 remains attached, keeping a closed circuit in the sensing wire. Alternatively, the sensing wire may be incorporated into the larger electrode 505, with an open circuit (from removing the liner 520) indicating an adult electrode configuration, and a closed circuit (from keeping the liner 520 attached) indicating a pediatric electrode configuration.

In all of the above embodiments, the sensing wire may be a physical strand of conductive material incorporated into the electrode arrangement. Alternatively, the wire may be formed from an etched or printed circuit line incorporated into the electrodes. Other sensing mechanisms for use in the present invention may include active electronics that determine and report which electrode is being used, or other passive mechanisms (e.g., measuring a change in inductance or capacitance from removal of one of the electrodes or nonconductive liners from the electrode arrangement).

Figure 11:
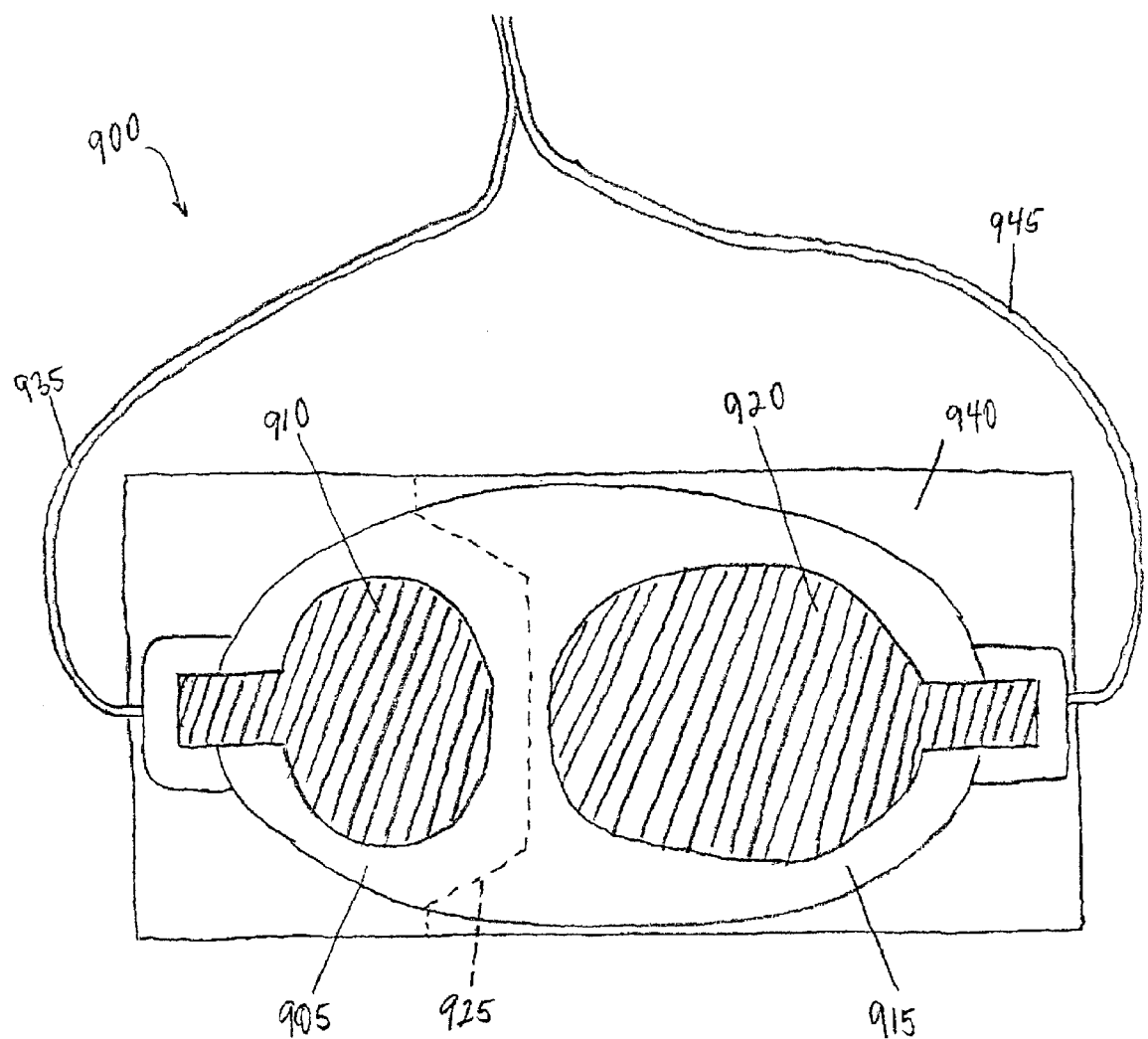
FIG. 11 is a plan view of an electrode arrangement configured according to yet a further embodiment of the present invention.

FIG. 11 illustrates yet another embodiment similar in form to the embodiment shown in FIG. 7. In FIG. 11, electrode arrangement 900 includes a first electrode 905 that is coplanar with and connected to second electrode 915. The first and second electrodes 905, 915 are separable along division line 925.

Conductive lead wire 935 is electrically connected to conductive surface area 910 that is centrally disposed on the first electrode 905. Similarly, lead wire 945 is electrically connected to conductive surface area 920 of the second electrode 915. The lead wires 935 and 945 are adapted to connect to an AED or other defibrillator or monitoring device. Initially, the lead wires 935, 945 may be electrically connected to one another, either in the device to which they are connected, or in a component (e.g., a switch) that selectively connects the lead wires. As discussed below, depending on which electrodes are used, the lead wires 935, 945 may be electrically separated from one another (if initially connected), with electrical energy being conducted to only one of the electrodes 905, 915.

In one suitable application, the conductive surface areas 910, 920 combined are each sized to provide a single adult electrode, while the conductive surface areas 910 or 920 alone are sized to provide a single pediatric electrode. Since, as illustrated, the conductive surface area 920 is larger than the conductive surface area 910, the second electrode 915 may be selected for larger pediatric patients and the first electrode 905 may be selected for smaller pediatric (e.g., infant) patients.

Further, an adhesive suitable for attachment to a patient is disposed on a portion of the electrode substrate outside the conductive surface areas 910, 920. A nonconductive release liner 940 is releasably attached to the conductive surface areas 910, 920 to prevent inadvertent attachment of the electrodes and to protect the conductive gel.

Adult defibrillation is provided by peeling away the release liner 940 from the electrodes, thus exposing the conductive surface areas 910, 920 which are placed on the patient. Defibrillation energy from an AED or other defibrillation device is then conducted through the lead wires 935, 945 to both conductive surface areas 910, 920 on the patient.

When pediatric defibrillation is desired, the first electrode 905 and the second electrode 915 are preferably separated from one another. The release liner 940 is removed from the electrode 905 or 915 selected for placement on the patient.

The defibrillation device to which the electrode arrangement 900 is connected is preferably configured to detect whether one or both of the electrodes 905, 915 have been placed on a patient. In that regard, the defibrillation device may communicate an impedance-sensing signal through the conductive surface areas 910, 920 of the two electrodes to determine whether one or both of the electrodes have been placed on a patient. Leads on/off circuitry that is present in conventional defibrillators may also be used to determine which electrodes have been applied to the patient.

When it is determined that only one of the electrodes 905 or 915 has been applied to a patient, the unapplied electrode may be electrically isolated from the applied electrode. In that regard, the defibrillation device detecting whether one or both of the electrodes have been applied to the patient may isolate the lead wire 935 or 945 that connects to the unapplied electrode.

With knowledge of which electrode has been placed on the patient, the defibrillation or monitoring device may modify its display in order to reflect the fact that pediatric or adult electrodes are in use. For a defibrillator, this improved monitoring or status display may be achieved without the defibrillation device altering the energy protocol delivered to the electrode arrangements. Energy attenuation may be provided in the pediatric electrode to scale the energy output from a therapy device for pediatric applications. See, e.g., the energy attenuator 450 in FIG. 5. Each state of a given electrode arrangement possesses an identifiable electrical impedance such that a compatible defibrillation device may distinguish between adult or pediatric electrodes being used for defibrillation.

The embodiments of the invention described herein are appropriate for electrode arrangements for both adult/pediatric or pediatric/neonatal configurations. For a pediatric/neonatal configuration, the larger electrode would be configured for a pediatric patient while the smaller electrode would be configured for a neonatal patient. Although the frequency of need for neonatal defibrillation electrodes is typically small, a pediatric/neonatal embodiment would be advantageous, for example, in a pediatric ward of a hospital.

Furthermore, electrode arrangements may be constructed in accordance with the present invention such that the electrodes in each arrangement are of substantially identical size, but attenuate the energy delivered from an AED or other defibrillation device differently. In this manner, one electrode in the electrode arrangement would deliver energy appropriate for pediatric defibrillation, while the other electrode in the electrode arrangement would deliver energy suitable for adult defibrillation. The electrode for pediatric defibrillation would normally transfer less energy to the patient than the electrode for adult defibrillation.

Figure 12:
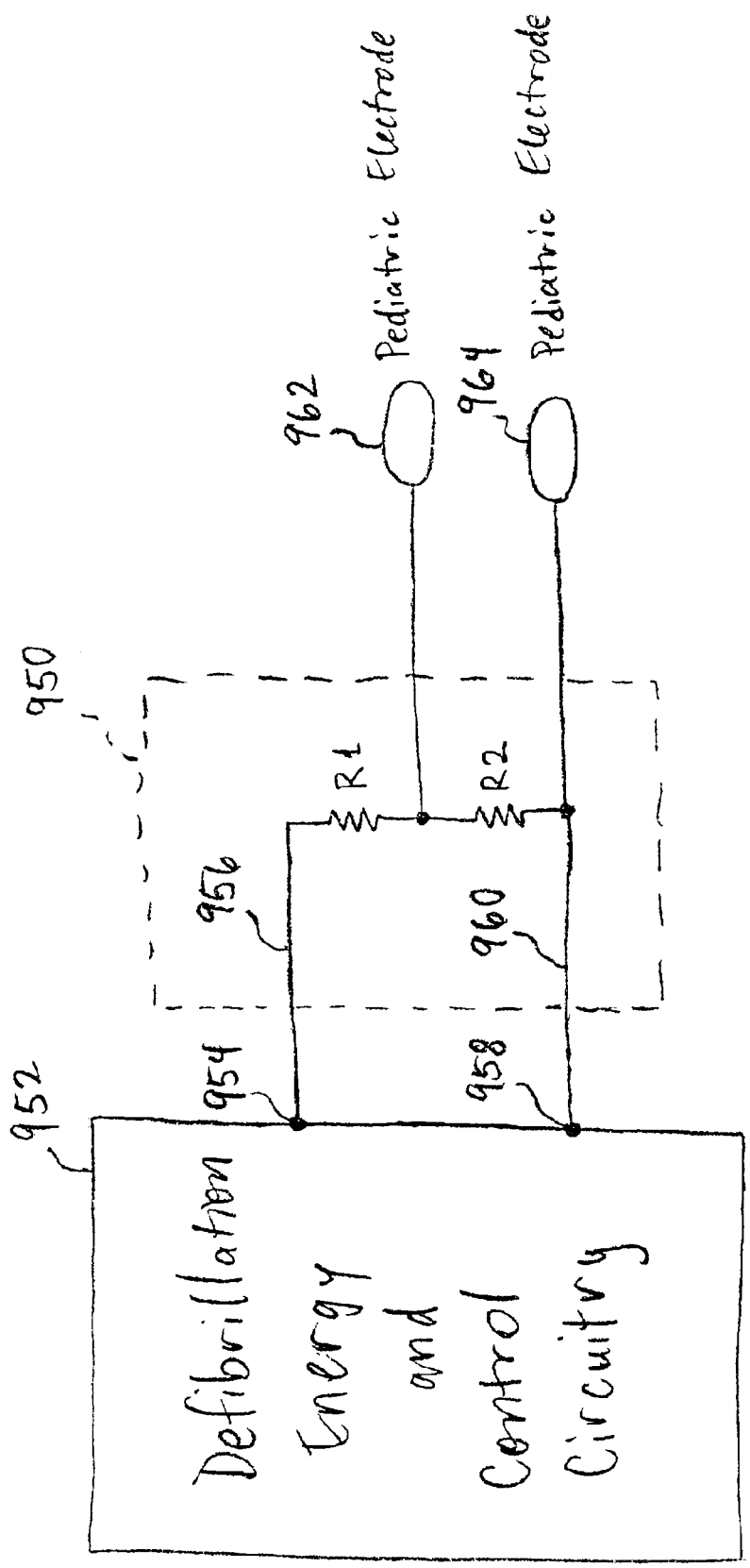
FIG. 12 is a schematic diagram of an energy attenuator for use in accordance with the present invention.

The energy attenuation in this aspect of the invention may be provided by a resistor network, as shown in FIG. 12. Energy attenuation may be provided by an energy attenuation circuit 950 that is used to dissipate a portion of the energy delivered from the defibrillation energy and control circuitry 952 so that a low energy pulse is delivered to a pediatric patient. In the particular embodiment shown in FIG. 12, two resistors R1 and R2 are connected to form an energy divider, with the pediatric electrode of each of the electrode arrangements to be placed on the patient being connected across one of the resistors. In FIG. 12, resistor R1 is coupled to an output port 954 of the defibrillation energy and control circuitry 952 by a coupler 956, while resistor R2 is coupled to an output port 958 by a coupler 960. The energy attenuation circuit 950 is coupled to pediatric electrodes 962 and 964 of two electrode arrangements provided by the present invention. The first pediatric electrode 962 is coupled to a circuit node between the resistors R1 and R2. The second pediatric electrode 964 is coupled to the other end of the resistor R2, which is connected to the output port 958. Suitable values for the resistors R1 and R2 range from 5 to 100 ohms in this embodiment of the invention. Other resistor values may be chosen for other embodiments of the invention.

As illustrated in FIG. 12, the resistors R1 and R2 are in series in a circuit path between the output ports 954 and 958, and the resistor R2 is in parallel with a patient (not shown) connected across the pediatric electrodes 962, 964. When the impedance of resistor R1 is significantly greater than the impedance of the patient, the resistor R1 will absorb most of the defibrillation pulse energy. The resistor R2, being in parallel with the patient, will absorb a portion of the energy in accordance with the current that flows through it rather than through the patient. The voltage drop across the resistor R2 and the patient will be approximately the same.

The resistance ratio of the two resistors R1 and R2 is preferably predetermined so that a predetermined percentage of the defibrillation energy from the defibrillation energy and control circuitry 952 is provided to the patient. The resistance values are determined according to a predetermined ratio so that in conjunction with the patient impedance, the energy delivered to the patient is scaled to a desired energy level. For example, the energy attenuation circuit 950 may have a 10:1 energy reduction ratio. Accordingly, energy delivered from the defibrillation circuitry 952 ranging from 2 joules to 360 joules would be reduced to energy ranging from 0. 2 joules to 36 joules. An isolation network (not shown) may also be connected to the energy attenuation circuit 950 to permit ECG signals to be more accurately monitored via the pediatric electrodes placed on the patient. Suitable energy attenuation circuits as described above are further described in copending application Ser. No. 09/684,506 titled ENERGY ADJUSTING CIRCUIT FOR PRODUCING AN ULTRA-LOW ENERGY DEFIBRILLATION WAVEFORM WITH FIXED PULSE WIDTH AND FIXED TILT, assigned to the assignee of the present invention, and incorporated by reference herein. Other energy adjusting circuits as described above are known in the art. See, e.g., U.S. Pat. Nos. 5,674,253 and 6,134,468, the disclosures of which are also incorporated by reference herein.

In embodiments of the invention described above, the two or more electrodes (or electrode regions) in each electrode arrangement are electrically connected to each other until the time of use when one or more of the electrodes may be selected for use and the other electrodes or electrode regions are removed. However, electrical connection between the electrodes (or electrode regions) is not necessary. For example, in reference to the electrode arrangement 900 shown in FIG. 11, the first electrode 905 may be connected via lead wire 935 to an AED (or other defibrillator or monitoring device) independent of the second electrode 915 and lead wire 945. It is further not necessary to the invention that the electrodes in each electrode arrangement be physically connected to each other, as shown in FIG. 11. Electrode arrangements with multiple electrodes that are not physically and electrically connected to each other may provide a user with additional flexibility in determining which electrodes in each electrode arrangement to place on a patient.

Figure 13:
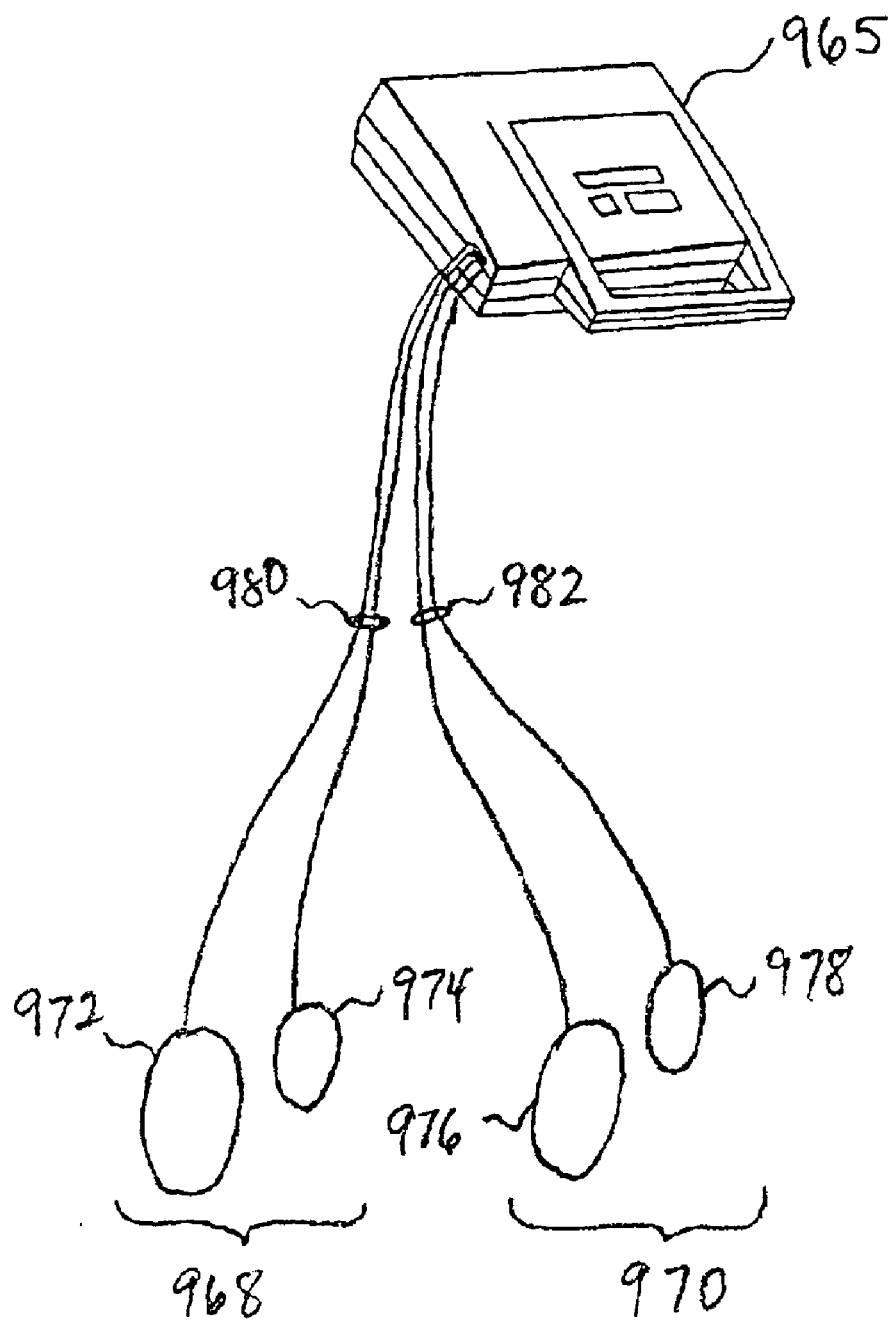
FIG. 13 is a pictorial diagram of a defibrillator with two electrode arrangements of the present invention connected thereto.

For example, FIG. 13 depicts a defibrillator 965 with two electrode arrangements 968 and 970 connected thereto. The electrode arrangement 968 is shown having two electrodes 972 and 974. The electrode arrangement 970 is shown having two electrodes 976 and 978. In each electrode arrangement 968, 970 as depicted, one of the two electrodes is larger than the other. The electrodes in the electrode arrangements 968, 970, which may be grouped and distinguished from each other by bands 980 and 982 around the respective lead wires, may be used in treating different patients, such as adult, pediatric, and infant patients.

In an exemplary application, the electrode arrangement 968 may be placed on the patient in an apex position while the electrode arrangement 970 may be placed on the patient in a sternum position. When the electrode arrangements 968, 970 are used on an adult patient, both electrodes in each of the apex 968 and sternum 970 arrangements are applied to the patient, for a total of four applied electrodes 972, 974, 976, 978. For a pediatric patient, only the larger electrodes 972, 976 of each of the apex 968 and sternum 970 arrangements are applied to the patient, for a total of two applied electrodes. Similarly, for an infant patient, only the smaller electrodes 974, 978 are applied, for a total of two applied electrodes. In other exemplary applications, the electrode arrangements 968, 970 may be configured so that the larger electrodes 972, 976 are used on adult patients and the smaller electrodes 974, 978 are used on pediatric or infant patients. It is also noted that an anterior-posterior electrode positioning may be used, particularly for very small children.

As noted earlier, an electrotherapy or monitoring device using electrode arrangements of the present invention may sense which of the electrodes in each electrode arrangement have been placed on the patient. A separate sensing element may be incorporated into the electrodes (e.g., as shown, for example, in FIGS. 7 and 8) or an electrical signal may be communicated from sensor circuitry in the device through the electrodes to detect a patient-electrode connection.

A sensor that uses an electrical signal to sense whether an electrode has been placed on the patient may communicate any form of electrical signal through the electrodes. Many conventional defibrillators already include circuitry that communicates an impedance-sensing signal through a patient to detect the patient's impedance. The circuitry that generates the impedance-sensing signal may be advantageously used in the present invention to also sense which electrodes have been placed on the patient. A signal generator of this type generally produces a low-amplitude, constant current, high-frequency signal (typically sinusoidal or square) having a frequency in the range of 10 kHz–100 kHz.

In a suitable embodiment of the invention, an electrotherapy or monitoring device senses which electrodes have been placed on the patient by communicating an electrical signal through each of the electrodes in a first electrode arrangement. If an electrical signal is not received by any of the electrodes in a second electrode arrangement, the device may conclude that at least one of the first or second electrode arrangements has no electrodes attached to the patient. In that regard, the device may prompt the user to finish connecting at least one electrode from each electrode arrangement to the patient.

Continuing with the foregoing example, if an electrical signal is successfully communicated from one electrode in the first electrode arrangement to an electrode in the second electrode arrangement, the device may conclude that those electrodes have been placed on the patient. The device continues by communicating the electrical signal through each of the electrodes in the first electrode arrangement, each time checking whether a signal is received by any of the electrodes in the second arrangement, to fully determine which electrodes in each electrode arrangement have been placed on the patient. In the context of the defibrillator system illustrated in FIG. 13, a suitable sensing algorithm may include communicating an electrical signal through electrode 972 while checking each electrode 976 and 978 to see if the electrical signal is received. The electrical signal is then communicated through the electrode 974, while electrodes 976 and 978 are again checked to see if the electrical signal has been received.

While the electrodes in an electrode arrangement may be substantially similar, it is advantageous for the electrodes in an electrode arrangement to differ from each other in respect of at least one characteristic of the electrodes. For example, the electrodes may differ in size, as shown in FIG. 13. Alternatively, the electrodes may be similar in size but have different size conductive surface areas on the electrode (e.g., one electrode with a larger conductive surface area than another electrode). The electrodes in an electrode arrangement may also differ in other electrode characteristics, such as an electrical parameter of the electrodes. In that regard, for example, one electrode may have a higher resistance than the other electrode (e.g., for attenuating energy intended for delivery to a pediatric patient).

The electrode arrangements are preferably configured so that corresponding electrodes (e.g., both larger or both smaller) in each electrode arrangement are placed on the patient. For example, where electrode arrangements with two electrodes are used in an apex and sternum configuration, either both electrodes, or the larger or smaller electrode, of each electrode arrangement are used on the patient. If three electrodes are sensed as being attached to the patient (e.g., both electrodes 972, 974 in the apex position and one electrode 978 in the sternum position), the electrotherapy or monitoring device using the electrode arrangements may detect this uneven number of electrodes as an improper combination of electrodes and report a fault condition to the user of the device. Suitable user outputs for reporting this and other information to the user include all forms of components capable of communicating information. Such components may comprise, without limitation, a display screen, LED lights, a speaker for audible output, a printer, etc. The electrotherapy or monitoring device may prompt the user to correct the situation by connecting the unapplied sternum electrode 976 or removing the apex electrode 972 that was improperly attached to the patient.

Other improper electrode combinations may also be detected and reported as a fault condition. For example, another improper combination may result from a larger electrode 972 in the apex position and a smaller electrode 978 in the sternum position. Upon sensing an improper electrode combination of this type, the device may prompt the user to correct the situation by ensuring that electrodes of the same size in each electrode arrangement 968, 970 are placed on the patient.

As noted earlier, one advantage of the present invention is that the electrotherapy to be delivered to a patient may be adjusted based on which electrodes in each electrode arrangement have been placed on the patient. In the foregoing example where both electrodes in the electrode arrangements 968, 970 are placed on a patient (generally signaling an adult patient), the defibrillator 965 may sense the electrode configuration and automatically deliver an energy dosage appropriate for an adult. Where only the larger or smaller electrode in each electrode arrangement 968, 970 is sensed as being placed on the patient (signaling a pediatric or infant patient, for example), an energy dosage appropriate for the pediatric or infant patient may be automatically delivered. Other aspects of the electrotherapy may be adjusted as well, such as the duration of the electrotherapy or the peak current or peak voltage delivered to the patient, based on which electrodes have been placed on the patient. Peak current and peak voltage may be adjusted by modifying the charge on a capacitor in the electrotherapy device that delivers the electrotherapy. Electrotherapy duration may be adjusted by modifying the timing of switches that connect and disconnect the capacitor from the electrodes placed on the patient. Where multiphasic electrotherapy pulses are delivered to the patient, the parameters of each phase of the delivered waveform may be independently adjusted based on the electrode configuration being used.

The electrotherapy or monitoring device may also determine and report a patient type via the user output based on the electrode combination sensed on the patient. For example, an "adult" patient type may be reported to the user if the device senses that both electrodes in a two-electrode arrangement have been placed on the patient. A "pediatric" or "infant" patient type may be reported if one or the other electrode in a two-electrode arrangement have been placed on the patient. The invention is not limited to "adult, " or "pediatric, " or "infant" patient types. Other patient types may be defined and named for reporting to the user of the device depending on the electrode combination being used.

While various embodiments of the invention have been illustrated and described above, it will be appreciated that various changes can be made therein without departing from the spirit and scope of the invention. Accordingly, the scope of the invention should be determined from the following claims and equivalents thereto.

The embodiments of the invention in which an exclusive property or privilege is claimed are defined as follows:

1. An electrotherapy apparatus, comprising:
   (a) two or more electrode arrangements, each electrode arrangement including a first electrode and a second electrode that each have a conductive surface area adapted for placement on a patient, either separately or in combination, wherein the conductive surface area of the second electrode is smaller than the conductive surface of the first electrode; and
   (b) electrotherapy circuitry in communication with the electrode arrangements, said circuitry being configured to deliver electrotherapy to the patient via the electrode arrangements after the first electrode, second electrode or combined first and second electrodes in each of the electrode arrangements has been placed on the patient.

2. The electrotherapy apparatus of claim 1, wherein one of the electrode arrangements is designated for an apex position on the patient and another electrode arrangement is designated for a sternum position on the patient.

3. The electrotherapy apparatus of claim 1, wherein one of the electrode arrangements is designated for an anterior position on the patient and another electrode arrangement is designated for a posterior position on the patient.

4. The electrotherapy apparatus of claim 1, wherein the electrodes in at least one of the electrode arrangements differ from each other in respect of a characteristic of the electrodes.

5. The electrotherapy apparatus of claim 4, wherein the characteristic is the size of the electrodes.

6. The electrotherapy apparatus of claim 4, wherein the characteristic is the size of the conductive surface area of the electrodes.

7. The electrotherapy apparatus of claim 4, wherein the characteristic is an electrical parameter of the electrodes.

8. The electrotherapy apparatus of claim 7, wherein the electrical parameter is resistance.

9. The electrotherapy apparatus of claim 1, further comprising a sensor in communication with the electrode arrangements, the sensor being configured to sense which of the first electrode, second electrode or combined first and second electrodes in each electrode arrangement has been placed on the patient.

10. The electrotherapy apparatus of claim 9, wherein the sensor is configured to communicate an electrical signal through the electrodes in the electrode arrangements to determine which electrodes have been placed on the patient.

11. The electrotherapy apparatus of claim 9, wherein the electrotherapy circuitry is further configured to adjust a parameter of the electrotherapy to be delivered to the patient based on which of the first electrode, second electrode or combined first and second electrodes in the electrode arrangements have been placed on the patient.

12. The electrotherapy apparatus of claim 11, wherein the parameter is a duration of the electrotherapy.

13. The electrotherapy apparatus of claim 11, wherein the parameter is a peak current of the electrotherapy.

14. The electrotherapy apparatus of claim 11, wherein the parameter is a peak voltage of the electrotherapy.

15. The electrotherapy apparatus of claim 11, wherein the parameter is energy to be delivered by the electrotherapy.

16. The electrotherapy apparatus of claim 9, wherein the electrotherapy circuitry is further configured to determine a patient type based on which of the electrodes in each electrode arrangement has been placed on the patient.

17. The electrotherapy apparatus of claim 16, further comprising a user output in communication with the electrotherapy circuitry, wherein the patient type is reported to a user of the electrotherapy apparatus via the user output.

18. The electrotherapy apparatus of claim 9, wherein the electrotherapy circuitry is further configured to determine whether the electrodes placed on the patient comprise an improper combination of electrodes.

19. The electrotherapy apparatus of claim 18, further comprising a user output in communication with the electrotherapy circuitry, wherein a fault condition is reported via the user output when an improper combination of electrodes has been placed on the patient.

20. The electrotherapy apparatus of claim 19, wherein art improper combination of electrodes is found on the patient when the electrodes placed on the patient from one electrode arrangement differ in an electrode characteristic from the electrodes placed on the patient from another electrode arrangement.

21. The electrotherapy apparatus of claim 20, wherein the electrode characteristic is the size of the electrodes.

22. The electrotherapy apparatus of claim 20, wherein the electrode characteristic is the size of the conductive surface area of the electrodes.

23. The electrotherapy apparatus of claim 20, wherein the electrode characteristic is an electrical parameter of the electrodes.

24. The electrotherapy apparatus of claim 20, wherein the electrode characteristic is the number of electrodes.

25. The electrotherapy apparatus of claim 1, wherein placement on the patient of one electrode in an electrode arrangement is mutually exclusive of placement of other electrodes in the same electrode arrangement.

26. The electrotherapy apparatus of claim 1, further configured to deliver electrotherapy to the patient through only one electrode in each electrode arrangement.

27. The electrotherapy apparatus of claim 1, further configured to deliver electrotherapy to the patient through more than one electrode in each electrode arrangement.

28. An electrotherapy method comprising:
(a) selecting at least one electrode from each of two or more electrode arrangements to be placed on a patient, wherein each electrode arrangement is comprised of a first electrode and a second electrode that each have a conductive surface area adapted for placement on the patient, either separately or in combination, wherein the conductive surface area of the second electrode is smaller than the conductive surface of the first electrode;
(b) placing the first electrode, second electrode or combined first and second electrodes on the patient; and
(c) delivering electrotherapy to the patient via the first electrode, second electrode or combined first and second electrodes placed on the patient.

29. The electrotherapy method of claim 28, further comprising sensing which of the first electrode, second electrode or combined first and second electrodes in each electrode arrangement have been placed on the patient and adjusting a parameter of the electrotherapy to be delivered to the patient based on which electrodes have been placed on the patient.

30. The electrotherapy method of claim 29, wherein the parameter is a duration of the electrotherapy.

31. The electrotherapy method of claim 29, wherein the parameter is peak current of the electrotherapy.

32. The electrotherapy method of claim 29, wherein the parameter is a peak voltage of the electrotherapy.

33. The electrotherapy method of claim 29, wherein the parameter is energy to be delivered by the electrotherapy.

34. The electrotherapy method of claim 28, further comprising sousing which of the first electrode, second electrode or combined first and second electrodes in each electrode arrangement have been placed on the patient by communicating an electrical signal through the electrodes in the electrode arrangements and determining which of the first electrode, second electrode or combined first and second electrodes have been placed on the patient based on the electrical signal.

35. The electrotherapy method of claim 28, further comprising sensing which of the first electrode, second electrode or combined first and second electrodes in each electrode arrangement have been placed on the patient and determining a patient type based on which of the first electrode, second electrode or combined first and second electrodes have been placed on the patient.

36. The electrotherapy method of claim 35, further comprising reporting the determined patient type.

37. The electrotherapy method of claim 28, further comprising sensing which of the first electrode, second electrode or combined first and second electrodes in each electrode arrangement have been placed on the patient and determining whether the electrodes placed on the patient comprise an improper combination of first electrode, second electrode or combined first and second electrodes.

38. The electrotherapy method of claim 37, further comprising reporting a fault condition if an improper combination of electrodes has been sensed.

39. The electrotherapy method of claim 38, wherein an improper combination of electrodes is sensed on the patient when the electrodes placed on the patient from one electrode arrangement differ in an electrode characteristic from the electrodes placed on the patient from another electrode arrangement.

40. The electrotherapy method of claim 39, wherein the electrode characteristic is the size of the electrodes.

41. The electrotherapy method of claim 39, wherein the electrode characteristic is the size of the conductive surface area of the electrodes.

42. The electrotherapy method of claim 39, wherein the electrode characteristic is an electrical parameter of the electrodes.

43. The electrotherapy method of claim 39, wherein the electrode characteristic is the number of electrodes.

44. The electrotherapy method of claim 28, wherein selection of one electrode in an electrode arrangement is mutually exclusive of other electrodes in the same electrode arrangement.

45. The electrotherapy method of claim 28, wherein electrotherapy is delivered to the patient through only one electrode in each electrode arrangement.

46. The electrotherapy method of claim 28, wherein electrotherapy is delivered to the patient through more than one electrode in each electrode arrangement.

* * * * *

UNITED STATES PATENT AND TRADEMARK OFFICE
CERTIFICATE OF CORRECTION

PATENT NO. : 6,912,425 B2
DATED : June 28, 2005
INVENTOR(S) : Nova et al.

It is certified that error appears in the above-identified patent and that said Letters Patent is hereby corrected as shown below:

Column 17,
Line 22, delete "art" and add -- an --.

Column 18,
Line 13, delete "sousing" and add -- sensing --.

Signed and Sealed this

Twenty-third Day of August, 2005

JON W. DUDAS
*Director of the United States Patent and Trademark Office*